United States Patent [19]

Fredericksen et al.

[11] Patent Number: 5,034,513
[45] Date of Patent: Jul. 23, 1991

[54] AVIAN INTERLEUKIN-2

[75] Inventors: Tommy L. Fredericksen, Cary, N.C.; Jagdev M. Sharma, Okemos, Mich.

[73] Assignee: The United States of America as represented by the Secretary of Agriculture, Washington, D.C.

[21] Appl. No.: 437,320

[22] Filed: Nov. 17, 1989

Related U.S. Application Data

[63] Continuation of Ser. No. 54,561, May 27, 1987, abandoned.

[51] Int. Cl.$^5$ .................. C07K 15/00; C12N 5/06
[52] U.S. Cl. .................. 530/351; 530/415; 530/416; 530/417; 530/827; 530/837; 435/70.1; 435/240.21; 435/240.22; 435/240.25
[58] Field of Search .............. 530/351, 415, 416, 417, 530/827, 837; 435/70.1, 240.21, 240.22, 241

[56] References Cited

U.S. PATENT DOCUMENTS 4,289,690 9/1981 Pestka et al. .................. 530/351
4,490,289 12/1984 Stern .................. 530/351

OTHER PUBLICATIONS

Schauenstein et al., CA, vol. 103, 1984, #121424v.
Schat et al., Avian Pathol 15(3), 1986, pp. 539–556 (abst).
Schauenstein et al., Dev. Comp. Immunol 7(4) 1983, pp. 267–268.
Giedlin et al., Lymphokine Res 3(4), 1984, p. 245.
Garland, J. M. and Hardie, Avril, "Relationship of Interleukin 3 to Lymphocyte Proliferation", Lymphokine Res. 3 (4), pp. 244–246 (1984).
Schauenstein, K., Kromer, G., Grinblat, J., Globerson, A., Trainin, N., and Wick, G., "Interleukin-2: Production, Autoimmunity and Aging", Top. Aging Res., 3 (Lymphoid Cell Funct. Aging), pp. 141–147 (1984).
Schat, K. A., Calnek, B. W., and Weinstock, D., "Cultivation and Characterization of Avian Lymphocytes with Natural Killer Cell Activity", Avian Pathology, 15, pp. 539–556 (1986).
Schauenstein, K. and Hayari, Y., "Avian Lymphokines", Development and Comparative Immunology, 7, pp. 767–768 (1983).
G. J. Fox et al., "Production of T Cell Growth Factor by Chicken Spleen Cells", Abstract of Paper Presented at 15th Southeastern Immunology Conference, Stone Mountain Inn, Ga., Oct. 20–22, 1982.
M. Schnetzler et al., "Characterization of Chicken T Cell Growth Factor", Eur. J. Immunol. 13: 560–566 (1983).
K. Schauenstein et al., "Avian Lymphokines: 1. Thymic Cell Growth Factor in Supernatants of Mitogen Stimulated Chicken Spleen Cells", Dev. Comp. Immunol. 6: 533–540 (1982).
O. Vainio et al., "Chicken T-Cell Growth Factor: Use in the Generation of a Long-Term Cultured T-Cell Line and Biochemical Characterization", Scand. J. Immunol. 23: 135–142 (1986).
G. Kromer et al., "Avian Lymphokines: An Improved Method for Chicken IL-2 Production and Assay. A Con A-Erythrocyte Complex Induces Higher T-Cell Proliferation . . . ", J. Immunol. Methods 73: 273–281 (1984).
S. Gillis, "Interleukin 2: Biology and Biochemistry", J. Clin. Immunol. 3(1): 1–13 (1983).
D. Riendeau et al., "Purification of Mouse Interleukin-2 to Apparent Homogeneity", Communication in J. Biol. Chem. 258(20): 12114–12117 (1983).

Primary Examiner—Garnette D. Draper
Attorney, Agent, or Firm—M. Howard Silverstein; Curtis P. Ribando

[57] ABSTRACT

A substantially pure species of avian Interleukin-2 has a molecular weight of about 30 kda. as determined by SDS-polyacrylamide gel electrophoresis. The compound is obtained from avian lymphocytes. It is produced by collecting lymphocytes from an avian donor, growing the lymphocytes in a medium containing a T cell mitogenic agent, and recovering the compound from the medium.

6 Claims, 1 Drawing Sheet

AVIAN INTERLEUKIN-2

This application is a continuation of application Ser. No. 07/054,561, filed May 27, 1987 now abandoned.

TECHNICAL FIELD

The present invention relates to a higher molecular weight species of avian Interleukin-2.

BACKGROUND OF THE INVENTION

The ability of various Interleukin-2 (IL-2) compounds to enhance an immune response has caused an enormous of commercial interest to focus on these compounds [see generally K. Welte and R. Mertelsmann, Cancer Investigation 3:35 (1985); M. H. Cheever et al., J. Biol. Resp. Modif. 3:462 (1984)]. The commercial aspects of this interest are reflected in the patent activity in this area: For example, U.S. Pat. No. 4,401,756 to Gillis discloses a process for preparing IL-2 from human malignant cells, U.S. Pat. No. 4,404,280 and 4,411,992 to Gillis disclose a process for producing murine (rat or mouse) IL-2 from malignant neoplastic cells, U.S. Pat. No. 4,448,879 to Fabricius and Stahn discloses a cell culture process for preparing serum-free and mitogen-free IL-2, U.S. Pat. No. 4,464,355 to Fabricius and Stahn discloses a serum-free and mitogen-free IL-2 derived from human, bovine, or porcine peripheral mononuclear blood cells, and U.S. Pat. No. 4,473,642 to Gillis discloses a process for producing murine IL-2 from hybridoma cells. These and other patents reflect the substantial importance of IL-2 compounds, and the importance of identifying additional IL-2 compounds to further expand the opportunities for their use.

IL-2, also referred to as T cell growth factor, is produced by activated T cells in response to antigenic stimulation, and is essential for the proliferation of activated T cells. IL-2 was first identified in the human system [D. A. Morgan et al., Science 193: 1007 (1976)], and has now been characterized in at least seven other mammalian species [L. S. English et al., Vet. Immunol. Immunopath. 9: 59 (1985)]. The size of the protein associated with naturally produced IL-2 varies, depending upon the animal species of origin. In human and rat, IL-2 is associated with a protein having a molecular weight of 15 kilodaltons (kda.) [S. Gillis et al., J. Immunol. 124: 1954 (1980); K. A. Smith et al., Mol. Immunol. 17: 579 (1980)], and in mouse with a protein having a molecular weight of 22 to 30 kda. [J. Watson et al., J. Exp. Med. 150: 849 (1979); D. Riendeau et al., J. Biol. Chem. 258: 12114 (1983)]. The cross species activity of IL-2 is variable, with human IL-2 having the broadest range in terms of its capacity to support the growth of activated T cells in other species, and with sheep IL-2 having the narrowest capability, supporting T cell growth only within its own species [P. Lindsay et al., in *Human Lymphokines. The Biological Immune Response Modifiers*, 479 (A. Kahn and N. Hill, eds., 1982); L. S. English et al., supra].

Several groups have begun to investigate avian IL-2 derived from activated avian T cells. K. Schauenstein et al. [Dev. Comp. Immunol. 6: 533 (1982)] were the first to present evidence for the presence of a T cell growth factor (an IL-2) in the supernatant of mitogen stimulated chicken spleen cells. While Schauenstein et al. did not purify this factor, it was observed that the chicken factor did not cross react with prestimulated murine lymphocytes, and that potent mouse T cell growth factor preparations did not exhibit a proliferative effect on chicken cells. After this development, Schauenstein's group disclosed an improved avian IL-2 production method [G. Kromer et al., J. Immunol. Methods 73: 273 (1984)].

Avian IL-2 activity has subsequently been suggested as associated with a 9–12 kda. protein by Schnetzler et al. [Eur. J. Immunol. 13: 560 (1983)], a 13-kda. protein by Vainio et al. [Scand. J. Immunol. 23: 135 (1986)], and a 19.5- to 21.5-kda. protein by Schnetzler et al., supra. The latter protein could be reduced to a 13-kda. molecule by SDS-polyacrylamide gel electrophoresis. It should be noted that the purified 13-kda. molecule described by Schnetzler et al. was not tested for IL-2 activity, and that Vainio et al. only show that IL-2 activity hovers around the 13-kda. region during Sephadex chromatography (see FIG. 3 therein). We now disclose the purification to homogeneity of a heretofor unknown species of avian IL-2 with a molecular weight of about 30 kda.

SUMMARY OF THE INVENTION

Figure 1:
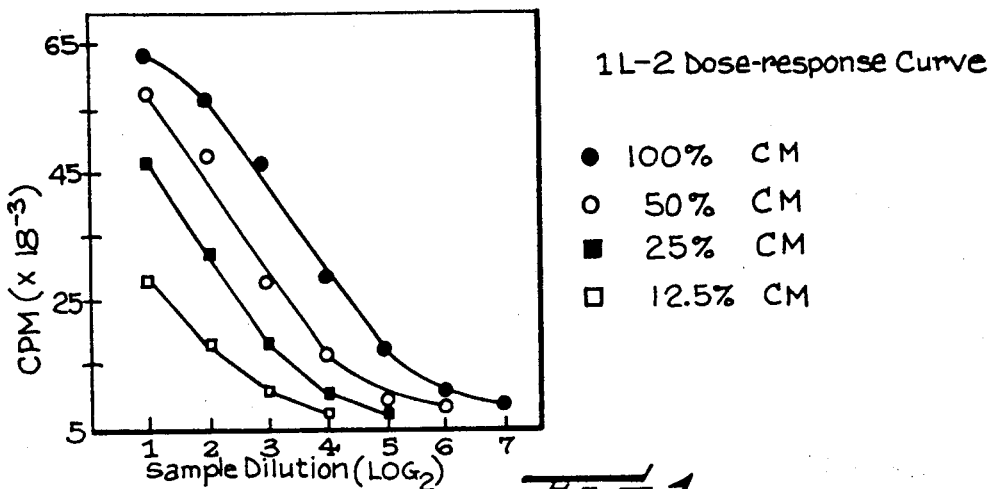
FIG. 1 is an IL-2 dose-response curve using 3-day Con A blast cells incubated with four different concentrations of the same conditioned medium.

We herein disclose a substantially pure avian Interleukin-2, having a molecular weight of about 30 kda. as determined by sodium dodecyl sulfate polyacrylamide gel electroporesis (SDS-PAGE) under reducing conditions. More particularly, we disclose a substantially pure proteinaceous factor which has a molecular weight of about 30 kda. (30±3 kda.) as determined by SDS-PAGE under reducing conditions, has a molecular weight of about 26 kda. (26±3 kda.) as determined by high resolution gel filtration chromatography, stimulates the growth of chicken Interleukin-2 dependent T cells in a dose-dependent manner, is heat stable at 40° C., and expresses low hydrophobicity in a phenyl-sepharose chromatography column. In this final property, the avian IL-2 disclosed herein differs from mouse IL-2, which can be separated on the basis of its hydrophobicity [see S. Gillis, J. Clin. Immunol. 3:1 (1983); D. Riendeau et al., J. Biol. Chem. 258:12114 (1983)]. Because of the charateristics of this compound, we have identified it as an IL-2. Those skilled in the art will appreciate, however, that it is the activity of the compound which is significant, and not the specific name assigned to it.

DETAILED DESCRIPTION OF THE INVENTION

The compound described above is obtained from avian lymphocytes. It is produced by collecting lymphocytes from an avian donor, growing the lymphocytes in a medium containing a T cell mitogenic agent, and recovering the aforesaid compound from the medium. In a preferred embodiment of the invention, the avian donor is a chicken, the medium in which the lymphocytes are grown is a serum-free medium, and the mitogenic agent is Concanavalin A (Con A). Further, in a preferred embodiment of the invention, the lymphocytes are collected from the spleen of an avian donor, though they could be collected by other means, such as by collecting peripheral white blood cells from an avian donor.

Also disclosed herein is a method of stimulating the growth of avian IL-2 dependent T cells. The method comprises mixing avian IL-2 dependent T cells in a nutrient media containing the compound described above in an amount sufficient to stimulate the growth of the avian IL-2 dependent T cells. This step is preferably carried out by suspending the cells in a culture media containing the aforesaid compound, and growing the cells therein. The term "avian," as used herein, is intended to encompass all avian species, including, for example, chickens, turkeys, ducks, geese, quail, and pheasant. A preferred species for carrying out the present invention is the chicken.

The primary component of the medium in which the avian lymphocytes are grown may consist of a commercially available medium, such as Roswell Park Memorial Institute (hereinafter "RPMI") medium, Dulbecco's Modified Eagle Medium, and Click's medium. Exemplary additives which may be individually or in combination added to the culture medium include penicillin, streptomycin, gentamicin, fresh glutamine, Hepes buffer, and chicken serum. T cell mitogenic agents which may be added to the medium include, for example, phytohemagglutinin and Con A.

EXAMPLE 1

Preparation of Conditioned Medium for Avian IL-2 Production

Specific pathogen-free inbred line $7_2$ (L7) chickens were hatched from eggs and reared in Horsfall Bauer isolator units under negative pressure. For most experiments, chickens were 3–10 weeks of age, and on occasion 11 to 28 weeks old.

A single-cell suspension was prepared from decapsulated chicken spleen in accordance with standard procedures. Specifically, the spleen was placed in phosphate buffered saline (PBS) (pH=7.4) passaged through a 5-ml. syringe barrel, and then passaged through an 18-gauge needle. The suspension was held at room temperature for 5 minutes to allow the stroma to settle, and the supernatant was collected. An additional 5 ml. of PBS was added to the settled stroma, mixed, held for 5 minutes, and the supernatant was collected and pooled with the first supernatant. These cells were then pelleted and washed twice with PBS before adding medium, as explained below. Cell viability was greater than 95% as measured by trypan blue dye exclusion.

Serum-free medium (RPMI-G) consisted of RPMI-1640 supplemented with L-glutamine (2 mM), and gentamicin sulfate (50 µg./ml.) (Sigma, St. Louis, MO). Medium with serum (RPMI-GS) consisted of RPMI-G and 1% heat inactivated chicken serum (CS) (Gibco, Grand Island, NY).

Single-cell suspensions from spleen were placed into a 75 cm.$^2$ flask with 50 ml. of medium at a cell concentration of $6 \times 10^6$ cells/ml. and a Con A (Calbiochem Behring Corp., La Jolla, CA.) concentration of 4–5 µg./ml. These concentrations were optimal for proliferation. Conditioned Medium (CM) was obtained from these cultures following incubation at 40° C. in a humidified atmosphere with 5% $CO_2$.

EXAMPLE 2

Production and Assay of Avian IL-2 in Conditioned Medium

Con A stimulated spleen cells, collected 3 days after culture initiation in RPMI-GS, concentrated by centrifugation, and fractionated on a 20–60% "Percoll" (Pharmacia, Piscataway, NJ) discontinuous gradient, were used as a source of IL-2 dependent T cells (IL-2 responder cells). RPMI-G was added to the final preparation and the cell suspension was adjusted to a concentration of $2 \times 10^6$/ml. in RPMI-G containing a final concentration of 0.05M alpha-methyl-D-mannoside (added to inactivate residual mitogen). Cells (0.1 ml.) were dispensed into 96-well microculture plates containing 0.1 ml. of serial twofold dilutions of sample IL-2. After 22 hours of incubation, 1 microcurie of ($^3$H)thymidine was added to each well, and the cultures were incubated for an additional 5 hours. A reference CM containing 1 U./ml. of IL-2 was included on each occasion. Cells were harvested on glass fiber paper with a Brandel M-24 cell harvestor, and the incorporated radioactivity was counted in "Liquiscent" medium (National Diagnostics, Sommerville, NJ) by a Beckman LS-100 liquid scintillation counter.

Regression analysis was used to define the dose-response curve between the growth of IL-2 responder cells and the concentration of IL-2 in sample CM. IL-2 activity was defined at the reciprocal titer that produced 50% of the maximum response, or the effective dose 50 ($ED_{50}$). Different preparations of CM containing IL-2 produced curves parallel to one another on most occasions. Comparisons of different CM for IL-2 were obtained from the proliferative response of CM at concentrations of 25% ($\log_2 2$) for low-titered CM and 10% ($\log_2 3.32$) for high-titered CM. The mean CPM response at this dilution of CM was then fitted to a line parallel to the laboratory standard and the difference in x-intercepts (extrapolated from both regression curves) were used to estimate the units of sample IL-2 activity. The laboratory reference standard was arbitrarily assigned an activity of 1 unit per milliliter (U./ml.). The maximum response to IL-2 in concentrated CM and to purified IL-2 obtained from hydrophobic chromatography was represented by the highest proliferation at the most concentrated dilutions.

As shown in FIG. 1, 3-day-old Con A stimulated spleen cells responded to IL-2 in CM in a dose-dependent manner. The growth curve was sigmoidal on a semi-log plot, and dilutions of the same sample gave curves that were lower and parallel to the growth curve of CM with the highest concentration of IL-2. Con A stimulated spleen cells from cultures containing serum-free medium (RPMI-G) did not always provide a reliable source of IL-2 responder cells. In an effort to improve upon this situation, Con A stimulated spleen cells were cultured in medium containing 1% chicken serum (RPMI-GS).

The cell yields from Con A stimulated spleen cells cultured in 75-cm.$^2$ flasks were higher in medium with RPMI-GS than those in RPMI-G. The geometric mean yield of cells per flask was $72.8 \times 10^6$ in RPMI-GS vs. $39.8 \times 10^6$ in RPMI-G (t=2.39, df=12, P<0.05). These responder preparations were then compared for sensitivity to IL-2 in CM (2 U./ml.) on the same occasions (see Table 1).

Con A spleen cells from RPMI-G medium usually had significantly higher levels of background proliferation than those from RPMI-GS (Table I, RPMI-G geometric mean CPM 2799 vs. 789 for RPMI-GS; t=2.81, df=21, P=0.01). Background proliferation was normally distributed following log transformation.

TABLE I

Characterization of IL-2 Sensitivity of Responder Cells from RPMI-GS or RPMI-G Medium to IL-2 in CM

| Experiment No. | Regression equation[a] (y = a + bx) | | Background (CPM) | | ED$_{50}$ (titer) | |
|---|---|---|---|---|---|---|
| | RPMI-GS | RPMI-G | -GS | -G | -GS | -G |
| 1 | 26,354 + (−4,204)x | 36,315 + (−4,358)x | 203 | 6,736 | 4.63 | 5.67 |
| 2 | 37,614 + (−5,038)x | 25,044 + (−3,248)x | 2,237 | 4,793 | 5.23 | 5.86 |
| 3 | 49,725 + (−6,857)x | 28,922 + (−3,717)x | 653 | 6,921 | 5.12 | 5.39 |
| 4 | 36,788 + (−4,972)x | 24,877 + (−3,548)x | 384 | 1,091 | 5.20 | 5.01 |
| 5 | 41,552 + (−6,700)x | 7,639 + (−1,186)x | 893 | 2,933 | 4.60 | 4.72 |
| Mean | | | 633 | 3,723[b] | 4.96 | 5.33 |
| IL-2 U./ml. | | | | | 2.1 | 3.6 |

[a]Linear curve CPM (CPM − background) plotted against log$_2$ dilution$^{-1}$
[b]Geometric means differ, P ≦ 0.05

The regression slopes were consistently higher when responder cells were obtained from RPMI-GS medium than from RPMI-G (t=3.08, df=8, P<0.05), providing for greater sensitivity. There were no differences in measurement of unit IL-2 activity by the two types of responder populations (2.1 U./ml. in RPMI-GS vs. 3.6 U./ml.; t=1.48, df=8). Increased yields of responder cells in RPMI-GS media, lower background proliferation, and similar sensitivity to IL-2 were major factors in selection of this culture medium for preparation of responder cells in the IL-2 assay.

Lower amounts of IL-2 were produced in Con A spleen cultures containing RPMI-GS medium than RPMI-G, and the production kinetics differed (see Table II).

Con A spleen cell cultures containing RPMI-GS achieved their maximum production of IL-2 at or before 25 hours of culture, while IL-2 production by Con A stimulated spleen cells in RPMI-G was increasing at 73 hours (Table III).

More IL-2 was synthesized in cultures containing RPMI-G medium. This culture preparation is useful for obtaining large quantities of IL-2, and does not contain serum factors.

EXAMPLE 3

Heat Stability of Avian IL-2

The stability of IL-2 in CM was tested following incubation at 40° C. for intervals ranging from 24 to 192 hours. CM used as controls were maintained at −20° C. prior to testing. Two preparations of CM containing IL-2 were used. One with unit activity of 1 and the other of 0.176 U./ml. CM containing 1 U./ml. showed no significant loss of activity after 120 hours of incubation (Table III). A similar absence of temperature effect on stability of IL-2 was observed in CM of 0.176 U./ml. (data not shown) following incubation for as long as 192 hours.

TABLE II

IL-2 Production by Con A Stimulated Splenic Lymphocytes In RPMI-GS and RPMI-G Medium

| IL-2[a] | Culture time (hrs.) | | |
|---|---|---|---|
| | 25 | 49 | 73 |
| RPMI-GS | 0.53 | 0.48 | 0.44 |
| RPMI-G | 3.50[b] | 4.34[b] | 5.60[b] |

[a]IL-2 U./ml., mean activity of 3 CM
[b]Columns differ, P ≦ 0.05

TABLE III

Influence of Temperature Upon IL-2 in Conditioned Medium Following Incubation

| | Log$_2$ dilution$^{-1}$ CM[a] | | | | Background |
|---|---|---|---|---|---|
| | 2 | 3 | 4 | 5 | |
| 40° C.[b] | 25,604[a] | 19,957 | 11,931 | 5,298 | |
| −20° C. | 28,180 | 22,089 | 12,543 | 5,279 | 580 |

[a]($^3$H)thymidine incorporation in CPM
[b]CM incubated for 5 days prior to testing for stability

EXAMPLE 4

Figure 2:
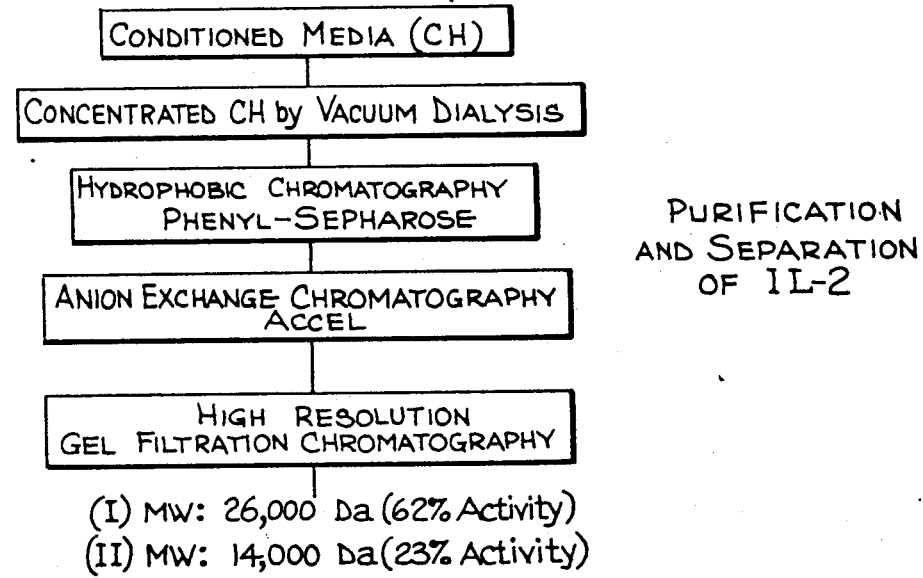
FIG. 2 shows the purification and separation protocol of IL-2 from conditioned medium of Con A activated spleen cells.

Partial Purification of Avian IL-2 from Conditioned Medium by Vacuum Dialysis and Hydrophobic Chromatography These procedures are diagrammed in the upper portion of FIG. 2. For each preparation, approximately 1 liter of CM was concentrated and dialyzed at 40° C. using a Micro-proDiCon vacuum dialyzer (Bio-Molecular Dynamics, Beaverton, OR) with a 10K MW exclusion membrane in 20 mM Tris buffer (pH=7.45). Solid ammonium sulfate (AS) was added to 8 ml. of concentrated CM to give a final salt concentration of 20% and applied to a 16×27 mm. column containing phenyl-sepharose CL-4B (Pharmacia) equilibrated with buffer containing 20% AS in 20 mM Tris (pH=7.45). Four-milliliter fractions were collected until no protein could be resolved. The column was then eluted stepwise with buffers containing decreasing concentrations of ammonium sulfate (AS) and increasing concentrations of ethylene glycol (EG) (% AS:% EG, 20:0, 20:10, 15:20, 10:30, 5:40, 0:50). Fractions were pooled to yield two fractions per elution buffer in approximately equal volumes, dialyzed against 20 mM Tris, and lyophilized. For tests of activity, the sample was reconstituted with 20 mM Tris, and the isotonicity of the buffer was adjusted with 10×PBS at the time of testing. Protein concentrations were determined by the Commassie dye binding microassay (Bio-Rad Laboratories, Richmond, CA).

IL-2 was not retained by the phenyl-sepharose gel in the 20% ammonium sulfate Tris starting buffer. Table IV provides the details of the actual recovery of IL-2 using this purification method. Sixty-seven percent of the starting protein was lost during concentration and dialysis of CM, and 43% of the IL-2 activity (Table IV) was recovered at the end of the purification process.

TABLE IV

Partial Purification of IL-2 in Conditioned Medium Using Phenyl-Sepharose

| Fraction | % AS:% EG | Total protein (mg.) | Total IL-2 (U.) | Recovery[a] (%) | SA[b] (U./mg.) | Purification |
|---|---|---|---|---|---|---|
| Crude CM | | 48.88 | 1,350 | — | 27.6 | 1 |
| Conc. CM | | 16.22 | 1,015 | 75.2 | 62.6 | 2.3 |
| (1)[c] | 20:0 | 1.04 | 418 | 31.1 | 401.9 | 14.6 |
| (2) | 20:10 | 0.18 | 16.6 | 1.2 | 92.2 | 3.3 |
| (3) | | 0.14 | 2.3 | 0.2 | 16.3 | 0.6 |
| (4) | 15:20 | 0.36 | 2.0 | 0.2 | 5.6 | 0.2 |
| (5) | | 0.39 | 0.7 | 0 | 1.8 | 0.1 |
| (6) | | 0.23 | 0 | 0 | 0 | |
| (7) | | 0.07 | 0 | 0 | 0 | |
| (8) | 10:30 | 1.78 | 1.4 | 0 | 1.8 | 0.1 |
| (9) | | 0.08 | 0 | 0 | | |
| (10) | 5:40 | 0.03 | 0 | 0 | | |
| (11) | | 0.11 | 0 | 0 | | |
| (12) | 0:50 | <0.03 | 0 | 0 | | |
| (13) | | <0.03 | 0 | 0 | | |
| (14) | Cold wash | <0.03 | 0 | 0 | | |
| (15) | 2 M Urea | <0.03 | 0 | 0 | | |
| (16) | 6 M Urea | <0.03 | 0 | 0 | | |

[a] Based on U. IL-2 in crude CM
[b] SA, specific activity
[c] Fraction number, elution by stepwise gradient A 14-fold purification was achieved for IL-2 yielding a specific activity of 401.9 U./mg.

EXAMPLE 5

Purification of Avian IL-2 to Homogeneity by Anion Exchange Chromatography, High Resolution Gel Filtration Chromatography, and Gel Electrophoresis These procedures are diagrammed in the lower portion of FIG. 2. Partially purified IL-2 obtained according to the procedure of Example 4 above, in 20 mM Tris buffer, pH=8.0, and was applied to an anion exchange column containing Accel medium (Millipore). The IL-2 passed through the column without binding. The fractions were dialyzed and then concentrated by vacuum dialysis (BioMolecular Dynamics) against 0.1M Tris buffer, pH=7.4. The most active fraction was applied to a Superose-12 (Pharmacia) high resolution gel filtration column (FPLC system, Pharmacia) equilibrated with 0.1M Tris buffer. Several applications were done, and similar fractions were pooled. The pooled fractions were concentrated to 1 ml. by vacuum dialysis. Molecular weight standards were run to establish an elution profile. The standards included ovalbumin-43 kda., carbonic anhydrase-29 kda., myoglobin-17.8 kda., and ribonuclease-13.7 kda. Protein concentrations were assayed by the Commassie dye binding microassay (Bio-Rad). Several Superose-12 fractions were then analyzed by SDS-polyacrylamide gel electrophoresis (SDS-PAGE) (12.5% gel) using a modification of the Laemmli method [see U.K. Laemmli, Nature 227:680 (1970)]. Silver staining was used to resolve the protein in these gels.

Figure 3:
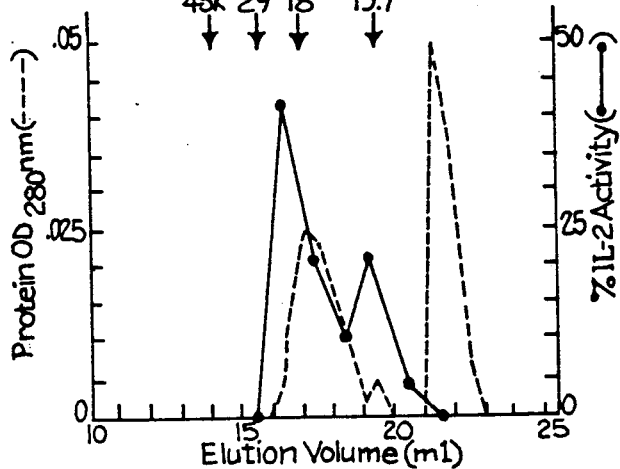
FIG. 3 is a high resolution gel filtration chromatogram of partially purified chicken IL-2.

Generally, the specific activity for IL-2 increased to an estimated activity of $10^4$ U./mg. following high resolution chromatography. A typical chromatogram and activity profile of the purification of IL-2 using a high resolution gel filtration column is illustrated in FIG. 3. The fraction with the greatest activity, fraction 16 (elution volume 16 to 17 ml.), had 42% of the total activity. A second peak of activity (23% of total) was resolved at an elution volume of 19-20 ml. These two peaks corresponded to two proteins having a molecular weight of about 26 kda. and about 14 kda., respectively.

Fraction 16 and 17 resolved a single band of protein identified by SDS-PAGE as having a molecular weight of about 30 kda. under reducing conditions. No bands of proteins could be identified in SDS-PAGE gels from elution volumes 19-20 ml., probably because of the low amount of protein present. Based on the gel analysis, nearly 63% of the total IL-2 activity was associated with the 30 kda. protein.

EXAMPLE 6

Assay of Purified Avian IL-2

The assay procedure used was the same as described in Example 2 above. One $ED_{50}$ of IL-2 activity was defined as the amount which in 1 ml. provides 50% maximum proliferative response of a Con A activated T cell population containing IL-2 responder cells.

Purified IL-2 from fractions 16 and 17 of the gel filtration chromatography procedure was tested for activity. The maximum growth induced was about 50% of the response observed for IL-2 in crude conditioned medium (Table V).

This may indicate that either the IL-2 responder population of Con A activated spleen cells contained other cells responding to other factors in crude conditioned medium, or some of the other factors enhanced the ability of IL-2 to promote proliferation.

Those skilled in the art will appreciate that the foregoing examples are illustrative of the present invention, rather than restrictive thereof. For example, lymphocytes may be obtained from different avian species, grown in media different from those specifically disclosed herein, grown in the presence of different media additives or mitogenic agents, and the avian IL-2 thus produced purified by different procedures. Accordingly, the scope of the present invention is to be determined from the following claims.

TABLE V

Growth Response of 3-Day-Old Con A Activated Spleen Cells to IL-2 in Conditioned Medium and to Purified IL-2

| Test | ED$_{50}$ CPM IL-2 source | | % Response[a] |
|---|---|---|---|
| | Conditioned medium (27 U./mg.) | Column purified (10$^4$ U./mg.) | |
| 1 | 24,108 | 10,447 | 43.3 |
| 2 | 11,003 | 6,343 | 57.6 |
| 3 | 9,280 | 5,204 | 56.1 |
| | | | 52.3 |

[a]ED$_{50}$ CPM response to column-purified IL-2 divided by response to IL-2 in conditioned medium

We claim:

1. Avian interleukin-2 as a homogeneous protein characterized by a molecular weight of about 30 (plus or minus three) kilodaltons as determined by SDS-polyacrylamide gel electrophoresis under reducing conditions, has a molecular weight of about twenty-six (plus or minus three) kilodaltons as determined by high resolution gel filtration chromatography, stimulates the growth of chicken Interleukin-2 dependent T-cells in a dose-dependent manner, is heat stable at forty degrees Centigrade, and expresses low hydrophobicity in a phenyl-sepharose chromatography column.

2. Chicken interleukin-2 as a homogeneous protein characterized by a molecular weight of about 30 (plus or minus three) kilodaltons as determined by SDS-polyacrylamide gel electrophoresis under reducing conditions, has a molecular weight of about twenty-six (plus or minus three) kilodaltons as determined by high resolution gel filtration chromatography, stimulates the growth of chicken Interleukin-2 dependent T-cells in a dose-dependent manner, is heat stable at forty degrees Centigrade, and expresses low hydrophobicity in a phenyl-sepharose chromatography column.

3. A substantially pure avian Interleukin-2 as claimed in claim 1 or 2 obtained from chicken lymphocytes.

4. A substantially pure avian Interleukin-2 as claimed in claim 1 or 2 which is produced by the process comprising collecting lymphocytes from an avian donor, growing the lymphocytes in a medium containing a T-cell mitogenic agent, and recovering the avian Interleukin-2 from the medium.

5. The substantially pure avain Interleukin-2 defined in claim 1 or 2 which is produced by the process comprising collecting lymphocytes from a chicken, growing the lymphocytes in a serum-free medium containing Concanavalin A, and recovering the avian Interleukin-2 from the medium.

6. A method of stimulating the growth of avian IL-2 dependent T-cells comprising mixing avian IL-2 as dependent T-cells in a nutrient media containing the Interleukin-2 as defined in claim 1 or 2 in an amount sufficient to stimulate the growth of the avian IL-2 dependent T-cells.

* * * * *